United States Patent [19]

Glazier

[11] Patent Number: 4,699,614
[45] Date of Patent: Oct. 13, 1987

[54] NON-REUSABLE SYRINGE

[76] Inventor: Stephen C. Glazier, 211 E. 35th St., Suite 8B, New York, N.Y. 10016

[21] Appl. No.: 21,657

[22] Filed: Mar. 4, 1987

[51] Int. Cl.[4] .............................................. A61M 5/00
[52] U.S. Cl. .................................... 604/110; 604/228
[58] Field of Search ............... 604/228, 110, 111, 218, 604/187

[56] References Cited

U.S. PATENT DOCUMENTS

| | | | |
|---|---|---|---|
| 3,754,644 | 8/1973 | Hampel | 604/228 X |
| 3,941,129 | 3/1976 | Pleznac | 604/111 |
| 4,252,118 | 2/1981 | Richard et al. | 604/228 X |
| 4,439,187 | 3/1984 | Butterfield | 604/111 |
| 4,507,117 | 3/1985 | Vining et al. | 604/228 X |

Primary Examiner—John D. Yasko
Attorney, Agent, or Firm—Dula, Shields & Egbert

[57] ABSTRACT

A non-reusable syringe comprising a barrel having an open end and a restricted end, a piston slidably positioned within the barrel and forming a liquid-tight seal with the interior of the barrel, a shaft freely slidable within the barrel and extending beyond one end of the barrel, a connector engaging the piston and the shaft and having a protrusion extending therefrom, and a guide formed on the shaft for receiving the protrusion of the connector. The connector is detachable form the shaft. The connector comprises a collar holder fastened at one end to the piston and a collar freely rotatable about the collar holder. The guide comprises a groove formed on the shaft which engages the protrusion from the collar. The guide causes the shaft to be disconnected form the connector following an injection of a liquid from the syringe.

19 Claims, 8 Drawing Figures

NON-REUSABLE SYRINGE

TECHNICAL FIELD

The present invention relates to syringes and more particularly to self-destructible or otherwise non-reusable disposable syringes.

BACKGROUND ART

Syringes are in common use today for hypodermic injection. Often these syringes are disposable syringes intended for only one use. However, these syringes are capable of repeated reuse if a user so desires. A serious problem today is that syringes are obtainable by intravenous drug addicts who repeatedly reuse and share the same syringe with other drug addicts without proper sterilization between each use. Hence, any blood-borne infectious disease that one such addict has is spread to those with whom he shares his syringes. This mechanism is thought to be a major cause of the spread of the current AIDS epidemic, as well as contributing to the spread of hepatitis, venereal disease, and other blood-borne diseases.

Recognizing the problem with the use of injectible drugs, several U.S. patents have addressed the problem by disclosing self-destructible syringes which render themselves unreusable.

U.S. Pat. No. 3,747,812, issued to Karman, et al. on July 24, 1973 discloses a syringe with a plunger shaft having a shear zone. This shear zone is utilized for breaking the shaft after a vacuum is produced following the withdrawal of fluids from a human body. To prevent reuse, the user of the syringe applies torque to the plunger, thereby breaking the shaft.

U.S. Pat. No. 3,478,937, issued to I, Solowey discloses a non-reusable syringe with a locking plunger. The upper end of the plunger has a collar unit which pushes through the collar at the top of the barrel on the downstroke. The collar expands, thereby locking the plunger and preventing reuse of this syringe after a single depression thereof.

U.S. Pat. Nos. 3,951,146; 3,998,224; and 4,391,273, issued to Chiquiar-Arias, disclose various forms of disposable, self-destructible syringes having blades attached to the piston which cut through the body of the syringe to prevent reuse, or sharp pins attached to the piston that puncture the body of the syringe.

U.S. Pat. No. 4,367,738, issued to Legendre, et al., discloses a non-reusable syringe having spikes attached to the shaft. The spikes pass inwardly through the body of the syringe and expand so as not to pass out backwardly.

Unfortunately, none of these prior-art patents have a feature in which the shaft of the plunger is disconnected from the piston of the syringe. In many cases, the disabling feature is not automatic. These prior-art devices allow the disabling feature to be neutralized by direct access or tampering prior to use. With these prior-art devices, the self-destructing feature is typically discretionary in the user.

It is an object of the present invention to provide a syringe that is self-destructing following a single use.

It is another object of the present invention to provide a self-destructible syringe that avoids tampering.

It is another object of the present invention to provide a disposable syringe to deter the spread of fatal infectious disease and to deter the theft and abuse of controlled substances.

It is still another object of the present invention to provide a self-destructible syringe that is relatively easy to manufacture, low in cost, and conventional in its single use.

These and other objects and advantages of the present invention will become apparent from a reading of the attached specification and appended claims.

DESCRIPTION OF THE INVENTION

The present invention is a non-reusable syringe that comprises a barrel having one open end and one restricted end, a piston slidably positioned within the barrel and forming a liquid-tight seal within the interior of the barrel, a shaft freely slidable within the barrel and having one end extending beyond the barrel, a connector engaging the piston and the shaft and having a protrusion extending therefrom, and a guide formed on the shaft and arranged so as to receive the protrusion of the connector. The connector is detachable from the shaft. The guide controls the movement of the piston relative to the movement of the shaft and includes means for causing the connector to detach from the shaft.

The connector includes a collar holder that is fastened at one end to the piston and a collar which is freely rotatable and mounted about the exterior of the collar. The collar has a protrusion extending outwardly therefrom. The collar holder has two parallel latitudinal ridges extending outwardly. These ridges have a diameter larger than the inner diameter of the collar. These ridges are arranged on opposite sides of the collar so as to restrict the longitudinal movement of the collar with respect to the collar holder. The collar specifically has two protrusions extending outwardly and equally spaced apart on the collar. These two protrusions engage the guide.

The guide of the present invention comprises a groove formed in the shaft and arranged so as to receive the protrusions of the collar. The collar holder has a diameter smaller than the cylindrical cavity. The protrusions are slidable within the the groove.

The groove has a Z-shaped configuration. This groove has an open end at the end of the shaft adjacent the restricted end of the barrel. This groove has a closed end at the opposite end of this Z-shaped configuration. This groove comprises a first portion that extends from the open end linearly and longitudinally aligned with the shaft, a second portion extending at an acute angle from the end of the first portion and extending toward the end of the shaft adjacent the restricted end of the barrel, and a third portion extending at an acute angle from the end of the second portion toward the open end of the barrel. The first portion of the groove has a constant width. The second portion of the groove has a constantly increasing width between the end of the first portion and the beginning of the third portion. The third portion has a generally constant width. The third portion extends from the second portion at an angle diagonal to the axis of the shaft. This third portion has a cul-de-sac end opposite the second portion. This Z-shaped groove occurs on opposite sides of the cylindrical cavity, and is aligned so as to properly receive the two protrusions of the collar.

The barrel of the present invention has a generally cylindrical configuration. The barrel's restricted end has suitable means for attaching a hypodermic needle thereto. The barrel further comprises a protruding rim formed inwardly at the open end of the barrel. This protruding rim defines an opening having a diameter greater than the diameter of the shaft. This protruding rim serves to restrict the further outward movement of the shaft from the barrel, once the end of the shaft adjacent to the restricted end of the barrel has approached the open end of the barrel.

The shaft has a protruding surface that is formed on the exterior of the shaft at the end of the shaft adjacent the restricted end of the barrel. This protruding surface has a size greater than the opening defined by the protruding rim of the barrel.

The collar holder of the present invention has a cavity formed in the end opposite the piston. An adhesive substance fills the cavity of the collar holder. A detachable cap is fastened to the top of the collar holder and covers the cavity. A filament has one end fixedly attached to the exterior of the detachable cap and the other end fixedly fastened to the interior of the shaft. After the connector detaches the shaft from the piston and when the shaft is withdrawn from the barrel as the piston remains in the barrel, the the filament causes the detachable cap to detach from the cavity and allows the adhesive to spill throughout the interior of the shaft. The adhesive is a non-viscous, quick-drying glue.

DETAILED DESCRIPTION OF THE INVENTION

Figure 1:
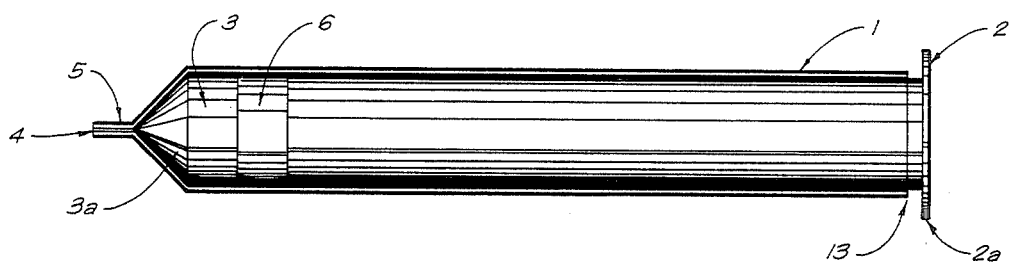
FIG. 1 is a cross-sectional view, in side elevation, showing the syringe of the present invention.

Referring to FIG. 1, there is shown the non-reusable syringe of the present invention. In particular, FIG. 1 shows the cylindrical barrel 1, cylindrical shaft 2, piston 3, restricted end 4 of barrel 1, open end 13 of barrel 1, and attachment section 5 for attaching a hypodermic needle or a tube to the syringe of the present invention. The connector system 6 of the present invention is illustrated in block form in FIG. 1.

As can be seen in FIG. 1, barrel 1 has a generally cylindrical configuration. Barrel 1 has an open end 13 through which the shaft 2 passes and a restricted end 4 through which liquids may pass. Hypodermic needles or tubes may be attached to the restricted end 4 of barrel 1.

Cylindrical shaft 2 acts as the plunger of the syringe of the present invention. Shaft 2 has a generally cylindrical or cruciform configuration and is closed at both ends. The outer diameter of shaft 2 is small than the inner diameter of barrel 1. Shaft 2 is freely slidable within barrel 1. As can be seen in FIG. 1, shaft 2 has a circular end cap 2a at the end of shaft 2 exterior of barrel 1.

Piston 3 is slidably positioned within the interior of barrel 1. Piston 3 forms a liquid-tight seal within the interior of the barrel. Piston 3 has an outside diameter slightly smaller than the inside diameter of barrel 1. This piston is slidable from one end of the barrel 1 to the other end. In assembly, piston 3 is inserted through the open end of barrel 1. Piston 3 has an end face 3a that is adjacent the restricted end 4 of barrel 1. End face 3a has a surface shape that exactly matches the surface shape of the inside surface of the restricted end 4 of barrel 1.

Figure 2:
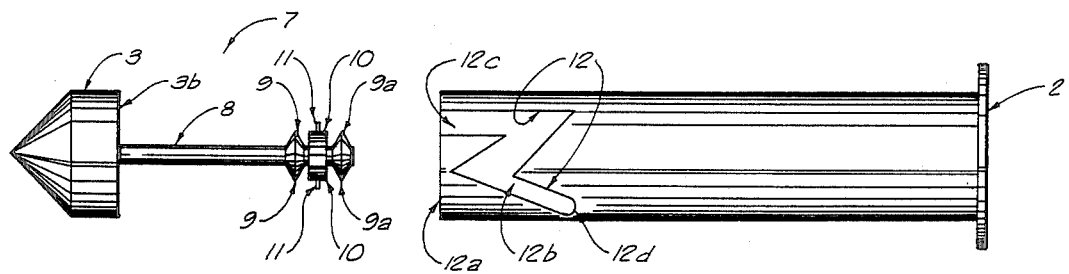
FIG. 2 is an exploded view of the present invention isolating the connector and guide system.

FIG. 2 shows a more detailed view of the connector system 7 and guide system 12 of the present invention. In operation, the connector system 7 engages the piston 3 and the shaft 2. In particular, connector system 7 includes a collar holder 8 fixedly attached to surface 3b of piston 3. Connector system 7 also includes an annular collar 10 that is freely rotatable about the exterior of collar holder 8. Collar 10 has two protrusions 11 on its outside surface. These protrusions 11 extend outwardly from collar 10 and serve to engage the guide system 12, to be described hereinafter.

Collar holder 8 has two parallel latitudinal ridges 9 and 9a. These ridges 9 and 9a extend outwardly from the exterior surface of collar holder 8. These ridges have a diameter larger than the inner diameter of collar 10. These ridges 9 and 9a are on opposite sides of collar 10 so as to restrict the longitudinal movement of the collar 10 with respect to the collar holder 8. The ridges 9 and 9a, collar 10 and protrusions 11 are arranged on collar holder 8 at the end opposite piston 3.

Figure 4:
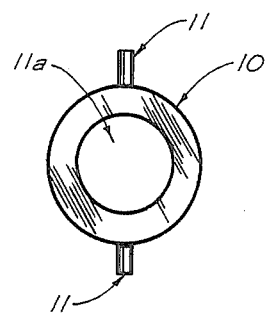
FIG. 4 is close-up top view of the collar of the present invention.
Figure 5:
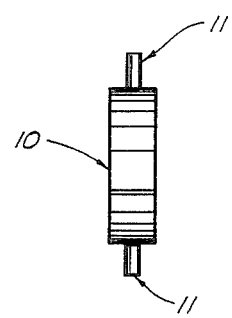
FIG. 5 is a side view of the collar of the present invention.

Referring to FIGS. 4 and 5, there is shown in greater detail the collar 10 and protrusions 11. These protrusions 11 are located on opposite sides and are equally spaced apart on collar 10. The interior 11a of collar 10 has a diameter slightly greater than the outer diameter of collar holder 8. This configuration allows the collar 10 to rotate freely with respect to the collar holder 8. Additionally, the inner diameter 11a of collar 10 is smaller than the diameter formed by the ridges 9 and 9a. Although the present invention shows two protrusions 11, it is believed possible that the present invention would operate equally well with one or more protrusions (and associated guide systems).

FIG. 2 shows the guide system 12 of the present invention. The guide system of the present invention is formed in shaft 2. Essentially a cylindrical cavity 12a is located within the shaft 2 in the end of the shaft nearest the restricted end 4 of barrel 1 such that the inner diameter of shaft 2 (which is the diameter of cavity 12a) is greater than the outside diameter of the collar holder 8, greater than the diameter of the peaks of the ridges 9 and 9a, greater than the diameter of the outside surface of collar 10, but less than the diameter of the circle defined by the ends of protrusions 11 on the exterior of collar 10, when the collar 10 is spun around about the axis of the collar holder 8.

Guide system 12 includes a groove 12b that is formed in shaft 2 and opens to the cylindrical cavity 12a. In the preferred embodiment of the present invention, there are two grooves formed in the shaft 12 of the present invention. The first groove is formed in the cylindrical cavity for receiving one of the protrusions 11 of the collar and a second groove is formed on the opposite side of the cylindrical cavity for receiving the other of the protrusions 11 of the collar 10. These grooves 12b are aligned with one another so as to allow the protrusions 11 to slide freely therethrough. Each of the grooves 12b should be of the same shape as the other grooves. The depth of the grooves should be such that the diameter of the barrel 1 from groove depth to groove depth is greater than the diameter of the circle described by the tips of the protrusions 11 on collar 10 when the collar 10 is spun around about the axis of the collar holder 8. The depth of these grooves 12b should be such that the collar holder 8 and the collar 10 can fit inside the cavity of the barrel 1, but only when each protrusion 11 enters into the open end 12c of a groove and slides inside a groove 12b. The minimum width of the grooves 12b is slightly greater than the width of each protrusion 11.

Each groove is a modified Z-shape. Each groove 12b has an open end 12c at the end of the shaft 2 adjacent the restricted end 4 of barrel 1. The groove has a closed end 12d at the opposite end of the Z-shaped configuration. These grooves 12b are arranged such that the collar may be aligned so that all the protrusions 11 match with one opening of a groove and the entire collar 8 and collar assembly may be inserted into the cylindrical cavity 12a.

Figure 3:
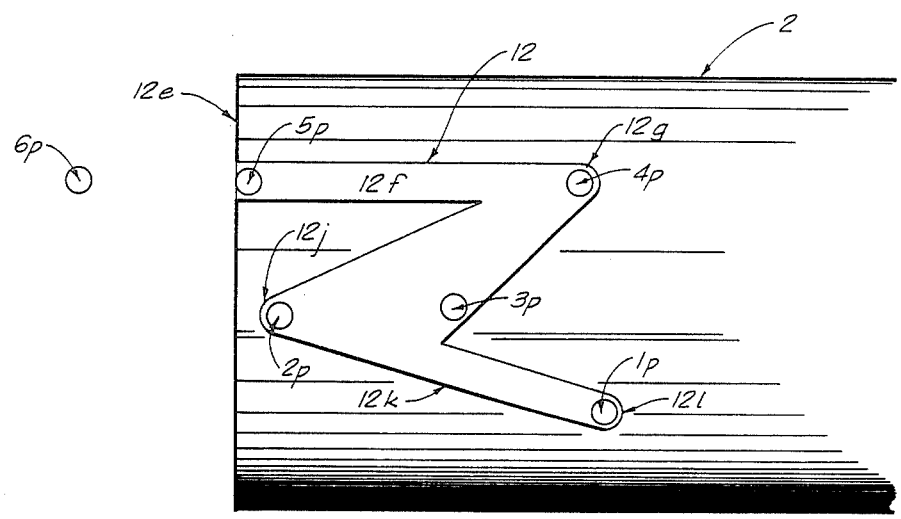
FIG. 3 is a close-up view of the guide system of the present invention.

The shape of the groove 12b is more specifically shown in FIG. 3. The groove 12b begins at the end 12c of shaft 2. As can be seen, groove 12b opens at end 12c. Groove 12b then forms a first portion 12f that travels straight back extending linearly from open end 12e and is longitudinally aligned with the shaft 2. First portion 12f has a generally constant width and extends to an acute angle corner 12g in the groove 12b. At the acute angle corner 12g, a second portion 12h of groove 12b is formed. This second portion 12h extends at an acute angle from the end 12g of first portion 12f and extends toward the end of shaft 2 adjacent the restricted end of barrel 1. The second portion 12h ends at an acute angle corner 12j. End 12j does not open at the end 12e but is a closed corner. A third portion 12k extends from corner 12j at the end of the second portion 12h and extends toward the open end of barrel 1. This third portion 12k extends from the second portion 12h at an angle diagonal to the axis of shaft 12. This third portion 12k has a cul-de-sac end 12l opposite corner 12j. In terms of shape, the first portion 12f of groove 12b has generally constant width. The second portion 12h of groove 12b has a constantly increasing width between the end 12g of first portion 12f and the end 12j of third portion 12k. Third portion 12k has a generally constant width.

It is through groove 12b that the protrusions 11 of collar 10 pass.

As shown in FIG. 3, the various positions of the protrusions 11 within groove 12b are shown. Initially, the syringe is delivered to the user such that the protrusion is in position 1. In position 1, the shaft may be compressed against the protrusion so as to push the piston 3 against the restricted end 4 of barrel 1. After the shaft 2 is compressed against the restricted end 4 of barrel 1, the shaft 2 must be pulled outwardly through the barrel 1. This will serve to draw fluid into the hypodermic needle and through the restricted end 4 of barrel 1. In order to draw the fluid into the barrel 1, the protrusion will move from position 1 to position 2 through groove 12k and to corner 12j. The protrusion 11 will abut corner 12j such that the outward movement of shaft 2 will cause piston 3 to be moved through the barrel 1 away from the restricted end 4. After fluid has been drawn into barrel 1, it will be necessary to compress the shaft 2 so as to deliver the fluid to a patient.

When the shaft 2 is compressed, protrusion 11 will move from position 2 to position 3. At position 3, the protrusion 11 will abut the wall of groove 12h. Protrusion 11 will then travel along the side of groove 12h until it reaches position 4 at corner 12g. At position 4, the compression of the shaft 2 will cause the piston 3 to move toward the restricted end 4 of barrel 1. It is this action that delivers the medication to the patient.

At this stage of the use of the syringe of the present invention, the protrusion 11 remains at position 4 and the piston 3 abuts the restricted end 4 of barrel 1. If a person desired to reuse the syringe following this step, it would be vitally necessary to be able to draw fluids into barrel 1 by pulling shaft 2 outwardly from barrel 1. Such a movement would cause protrusion 11 to move from corner 12g (and position 4) through groove 12f. Ultimately, the protrusion 11 would exit the groove 12 by passing to position 5 and position 6. At all times, the piston 3 would remain in abutment with the restricted end 4 of barrel 1. Since the protrusion 11 would not abut another surface, the piston could not be drawn away from the restricted end 4.

When the protrusion 11 is at position 6, the protrusions 11, collar 10 and associated collar holder 8 are disconnected from the shaft 2. This disconnects the shaft 2 from the piston 3 such that the shaft 2 may be pulled out of the open end of barrel 1 without causing the piston 3 to move toward the open end 13 of barrel 1. Although the shaft 2 may be reinserted end 4 of barrel 1, it may only further push the piston 3 toward the restricted end 4 of barrel 1. It would not cause the piston 3 to move toward the open end 13 of barrel 1. This syringe is thus rendered unable to be filled with a second load of fluid for a second injection and thus is rendered non-reusable after it is filled and emptied once and only once.

The rotatable positioning of the collar 10 on collar holder 8 causes the collar to remain free to spin. The shaft 2 is restricted from turning inside the barrel 1 so that the protrusions 11 cannot be made to retrace their path in the grooves 12b back to the position 1.

Figure 6:
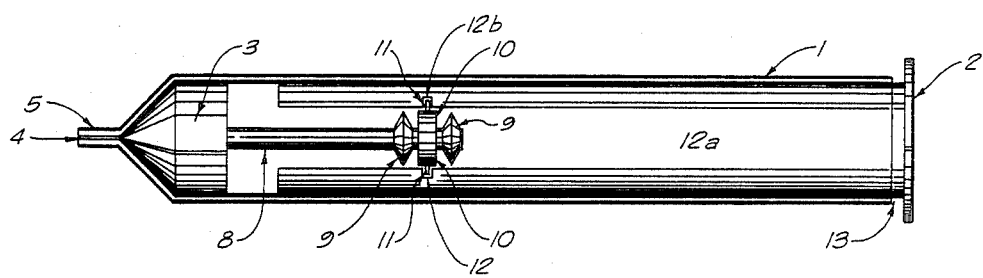
FIG. 6 is a cross-sectional view of the syringe of the present invention as assembled before use.

FIG. 6 illustrates the configuration of the syringe of the present invention in its assembled condition prior to use. In order to draw fluids into the restricted end 4, it is necessary to pull shaft 2 outwardly from barrel 1 so as to cause the protrusions 11 to shift from position 1 to position 2. It can also be seen in FIG. 6 that the diameter about ridges 9 is smaller than the inner diameter of cylindrical cavity 12a of shaft 2.

Figure 7:
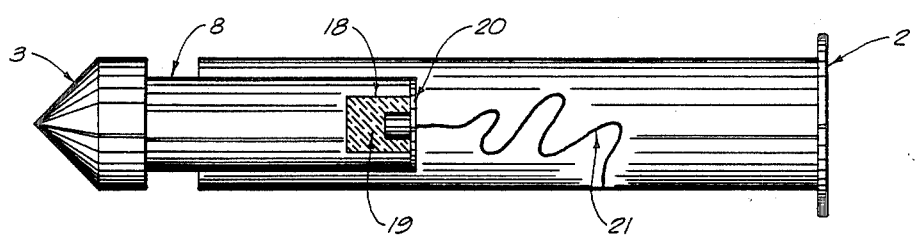
FIG. 7 is a cross-sectional view of an alternative embodiment of the present invention, isolating the cap, glue cavity, and filament.

FIG. 7 shows an alternative embodiment of the present invention. In this alternative embodiment of the present invention, the collar holder 8 has a cylindrical cavity 18 formed at the end of collar holder 8 opposite positon 3. A liquid adhesive 19 fills cavity 18 within collar holder 8. A detachable cap 20 covers the cavity 18 of collar holder 8. Ideally, cap 20 maintains a liquid-tight engagement with cavity 18 so as to prevent the adhesive 19 from spilling out. Ideally, adhesive 19 is a quick-drying, non-viscous liquid. The detachable cap 20 has a diameter equal to the diameter of the collar holder 8. The detachable cap 20 is fastened over the cavity 18 so as to be flush with the exterior surface of collar holder 8. A filament 21 has one end fixedly attached to the exterior of the detachable cap 20. The other end of filament 21 is fixedly fastened to the interior of shaft 2 and is located distal from the guide system.

In operation, when the shaft 2 is pulled toward the end of barrel 1, and the piston 3 does not move, the filament 21 (or fiber) becomes taut. This pulls the cap 20 from the cavity 18. The glue 19 then spills out of the cavity 18 and contacts the outside of the collar holder 8, the collar 10, and the inside surface of the barrel 1. This serves to fuse all these parts into one immobile piece so that the piston 3 may not be accessed and functioned, by the shaft 2, or by any other implement or means should the shaft be removed from the barrel or otherwise.

Figure 8:
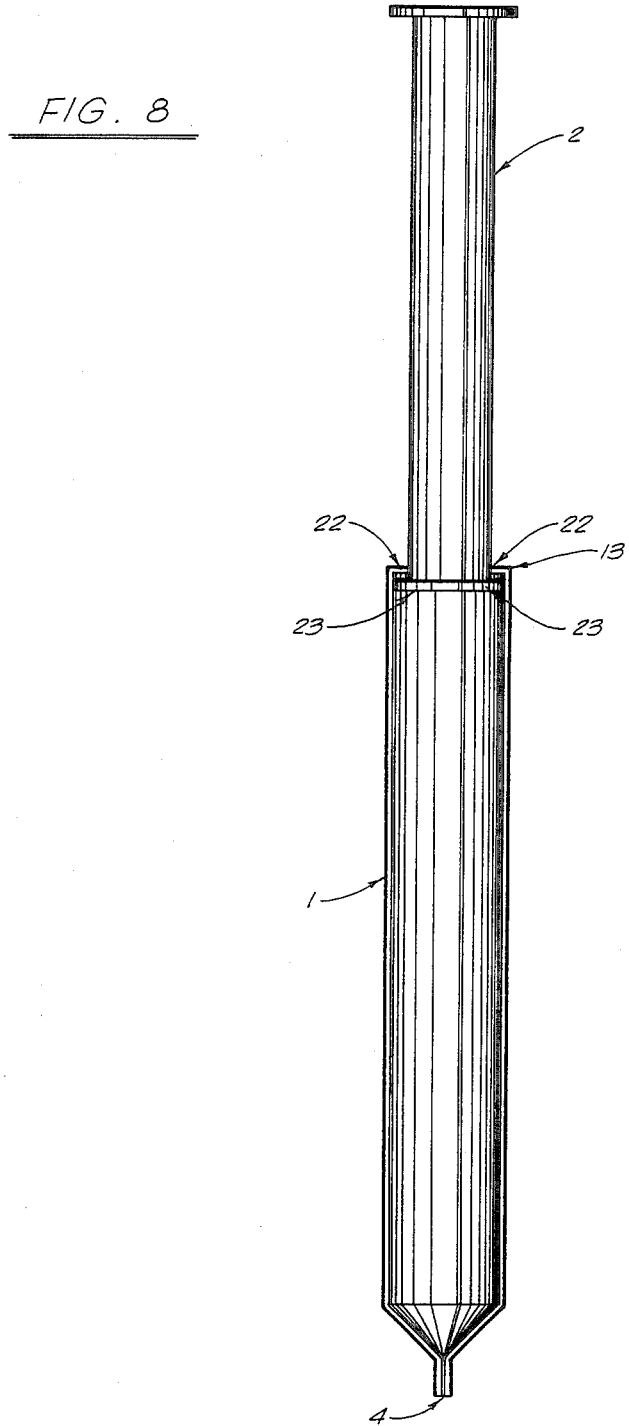
FIG. 8 is a cross-sectional view showing a modification to the embodiment of the present invention.

FIG. 8 shows a further improvement of the present invention which prevents the shaft 2 from easily being removed from the interior of barrel 1. In the embodiment shown in FIG. 8, a protruding rim 22 is formed inwardly at the open end 13 of barrel 1. This protruding rim defines an opening having a diameter greater than the diameter of shaft 2. This protruding rim 22 restricts the outward movement of the shaft 2 from the barrel 1. In addition, shaft 2 has a protruding surface 23 formed on the exterior of shaft 2 at the end of the shaft adjacent the restricted end 4 of barrel 1. This protruding surface 23 has a diameter greater than the opening as defined by the protruding rim 22. The protruding rim 22 on the opening at the open end 13 of barrel 1 constricts the opening so as to not inhibit the sliding of the shaft 2 in and out of the barrel 1. However, protruding rim 22 will contact the protruding surface 23 on the outside surface of shaft 2. In this manner, after the shaft 2 is inserted into the barrel 1, the shaft 2 may not again be removed from the barrel 1, so that the connector system 6 may not be accessed for modification or tampering with glue or other means.

The present invention separates the conventional shaft (or plunger end) of typical syringes, into two separate parts. First, a piston with sealing surfaces and, second, a separate shaft to reach and move the piston inside the barrel. The separate shaft and piston of the present invention are connected by a connector system that automatically connects the piston with the shaft during one use, and then permanently and destructively disconnects the piston from the shaft. In this manner, the shaft may not reconnect to the piston to draw it back to refill the barrel for a second use. The piston is immobile and fused to the barrel. The connector disconnects after the piston is drawn back to fill the barrel and then is pushed in to empty the barrel. In the present invention, the shaft cannot be reconnected with the piston to redraw it to refill the barrel for reuse.

The present invention provides a safe and automatically self-destroying syringe. Since the syringe of the present invention can only be used one time, it serves to deter the spread of fatal infectious disease and to deter the theft and abuse of controlled substances. The present invention eliminates the possibility of sharing and reusing a contaminated syringe. The configuration of the present invention offers a cost-effective alternative to present syringes and offers a technique that is easy to manufacture and easy to implement. No additional instruction will be required to enable a physician to properly use the present invention.

The embodiments as illustrated and discussed in this specification are intended only to teach those skilled in the art the best way known by the inventor to make and use the invention. Nothing in the specification should be considered as limiting the scope of the present invention. Many changes could be made by those skilled in the art to produce equivalent systems without departing from the invention. The present invention should only be limited by the following claims and their legal equivalents.

I claim:

1. A non-reusable syringe comprising:
   a barrel having one open end and one restricted end through which a liquid may pass;
   a piston slidably positioned within said barrel, said piston forming a liquid-tight seal with the interior of said barrel;
   a shaft freely slidable within said barrel, said shaft extending beyond one end of said barrel;
   connector means engaging said piston and said shaft, said connector means having a protrusion extending therefrom, said connector means detachable from said shaft; and
   guide means formed on said shaft, said guide means receiving said protrusion of said connector means, said guide means for controlling the movement of said piston relative to the movement of said shaft, said guide means causing said connector means to detach from said shaft.

2. The syringe of claim 1, said connector means comprising:
   a collar holder fastened at one end to said piston; and
   a collar freely rotatably mounted about the exterior of said collar holder, said collar having said protrusion extending outwardly therefrom, said guide means formed on the interior of said shaft.

3. The syringe of claim 2 said collar holder having two parallel latitudinal ridges extending outwardly, said ridges having a diameter larger than the inner diameter of said collar, said ridges being on opposite sides of said collar so as to restrict the longitudinal movement of said collar with respect to said collar holder.

4. The syringe of claim 2, said collar having two protrusions extending outwardly and equally spaced apart on said collar.

5. The syringe of claim 4, said two protrusions engaging said guide means.

6. The syringe of claim 2, said guide means comprising:
   a cylindrical cavity interior of said shaft at the end of said shaft adjacent said restricted end of said barrel; and
   a groove formed in said cylindrical cavity, said groove for receiving said protrusion of said collar, said collar holder having a diameter smaller than said cylindrical cavity, said protrusion slidable within said groove.

7. The syringe of claim 6, said groove having a Z-shaped configuration, said groove having an open end at the end of said shaft adjacent said restricted end of said barrel, said groove having a closed end at the opposite end of said Z-shaped configuration.

8. The syringe of claim 7, said groove comprising:
   a first portion extending from said open end linearly and longitudinally aligned with said shaft;
   a second portion extending at an acute angle from the end of said first portion and extending toward the end of said shaft adjacent said restricted end of said barrel; and
   a third portion extending at an acute angle from the end of said second portion and toward said open end of said barrel.

9. The syringe of claim 8, said first portion of said groove having a constant width, said second portion of said groove having a constantly increasing width between the end of said first portion and the beginning of said third portion, said third portion having a generally constant width.

10. The syringe of claim 8, said third portion extending from said second portion at an angle diagonal to the axis of said shaft, said third portion having a cul-de-sac end opposite said second portion.

11. The syringe of claim 5, said guide means comprising:
- a cylindrical cavity interior of said shaft at the end of said shaft adjacent the restricted of said barrel;
- a first groove formed in said cylindrical cavity for receiving one of said protrusions of said collar; and
- a second groove formed on the opposite side of said cylindrical cavity for receiving the other of said protrusions of said collar, said protrusions freely slidable within said first and second grooves.

12. The syringe of claim 1, said barrel having a generally cylindrical configuration, said restricted end having a means for attaching a hypodermic needle.

13. The syringe of claim 12, said barrel further comprising:
- a protruding rim formed inwardly at said open end of said barrel, said protruding rim defining an opening having a diameter greater than the diameter of said shaft, said protruding rim restricting the outward movement of said shaft from said barrel.

14. The syringe of claim 13, said shaft further comprising:
- a protruding surface formed exterior of said shaft at the end of said shaft adjacent said restricted end of said barrel, said protruding surface having a size greater than said opening defined by said protruding rim.

15. The syringe of claim 2, said collar holder having a cavity formed in the end opposite said piston, said connection means further comprising;
- a detachable cap covering said cavity of said collar holder;
- a filament having one end fixedly attached to the exterior of said detachable cap and the other end fixedly fastened to the interior of said shaft distal from said guide means; and
- an adhesive filling said cavity of said collar holder.

16. The syringe of claim 16, said cavity of said collar holder being cylindrical, said detachable cap having a diameter equal to the diameter of said collar holder, said detachable cap fastened over said cavity so as to be flush with the exterior surface of said collar holder.

17. The syringe of claim 15, said adhesive comprising a non-viscous, quick drying glue.

18. The syringe of claim 1, said piston having an end facing said restrictive end of said barrel, said end having a shape matching the shape of the inside surface of said restricted end of said barrel.

19. The syringe of claim 1, said shaft having a cylindrical exterior configuration, said shaft having a circular end cap at the end exterior of said barrel, said circular end cap having a size greater than the cross-sectional size of said shaft.

* * * * *